United States Patent [19]

Ott

[11] Plant 4,593

[45] Sep. 23, 1980

[54] POINSETTIA

[76] Inventor: Cleveland Ott, 677 Grater Ave., Graterford, Pa. 19426

[21] Appl. No.: 2,259

[22] Filed: Jan. 10, 1979

[51] Int. Cl.[3] ..... A01H 5/00
[52] U.S. Cl. ..... Plt./86
[58] Field of Search ..... Plt./86

*Primary Examiner*—Robert E. Bagwill
*Assistant Examiner*—James R. Feyrer
*Attorney, Agent, or Firm*—Paul & Paul

[57] ABSTRACT

A new and distinct variety of poinsettia plant is a sport of Annette Hegg Supreme (U.S. Plant Pat. 3,392). The new variety is characterized by bracts which are distinctly rugose. The leaves, however, are not rugose. The bracts are light pink but the venation is dark rose and prominent. The bracts are not lobed. The bracts are more round and less pointed than in the parent. The foliage is a lighter green than in the parent.

1 Drawing Figure

ORIGIN OF THE VARIETY

The new variety of poinsettia plant was discovered by applicant as a sport in a bed of Annette Hegg Supreme poinsettias (U.S. Plant Pat. No. 3,392) in applicant's greenhouse near Graterford, Pa. This discovery was made in December 1976 but none of the new variety plant was sold or offered for sale until December 1978.

Asexual Reproduction of the Variety

Following applicant's discovery, applicant asexually reproduced the new and distinct variety in his greenhouse by the rooting of cuttings from the new sport. The asexually reproduced poinsettia plants have uniformly new and distinct characteristics.

SUMMARY OF THE VARIETY

The new and distinct variety of poinsettia plant is characterized by the following features.

(1) The bracts are pink, a lighter pink than the parent. The pink color of the bract is deeper with greater illumination, and paling with less illumination, as for example, when the bract is shaded. The closest designation on the Royal Horticultural Society (RHS) Color Chart is near 52D when fully illuminated, the color paling when shaded. On the Horticultural Color Chart (HCC) the closest designation is HCC 621 when the bract is fully illuminated, paling to HCC 621/3 when shaded.

(2) The veins are dark rose. The closest designation of the vein color on the Royal Horticultural Society (RHS) color chart is 46D which, according to the RHS Color Chart Table of Cross References corresponds to Delft Rose HCC 020, on the Horticultural Color Chart (HCC).

(3) The bracts are rugose, i.e. the bracts are puckered.

(4) The bracts are arched from edge to edge.

(5) The bracts are non-lobed and are round and less pointed than in the parent.

(6) Some of the bracts are twisted on their stems.

(7) The plant is self-branching.

BRIEF DESCRIPTION OF THE DRAWING

The drawing comprises a photographic reproduction in color of the new and distinct poinsettia plant of this application. The color of the bracts in the photograph is as nearly true as it is reasonably possible to make the same in a color illustration of this character.

DETAILED DESCRIPTION OF THE VARIETY

The new and distinct variety of poinsettia plant of this application was asexually reproduced from a sport of Annette Hegg Supreme poinsettia (U.S. Plant Pat. No. 3,392).

The bracts are pink, a lighter pink than the parent. The pink color of the bract is deeper with greater illumination, and paling with less illumination, as for example, when the bract is shaded. The closest designation on the Royal Horticultural Society (RHS) Color Chart is near 52D when fully illuminated, the color paling when shaded. On the Horticultural Color Chart (HCC) the closest designation is HCC 621 when the bract is fully illuminated, paling to HCC 621/3 when shaded.

The veins are rose color. The venation is substantially darker than the lighter pink of the remainder of the bract. The closest designation of the color of the veins on the Royal Horticultural Society (RHS) color chart is 46D which, according to the RHS Color Chart Table of Cross References corresponds to Delft Rose HCC 020 on the Horticultural Color Chart (HCC).

The outstanding characteristics of the new variety of poinsettia plant is that the bracts are rugose. That is to say, the veins lie in valleys on the upper surface of the bracts and the epidermis is arched between the veins.

The bracts are arched between opposite edges.

The bracts are non-lobed and are more round and less pointed than the parent.

The plant is self-branching.

In some of the new variety of plant, but not in all, the bract stem is longer than in the parent, and the composite flower is less compact than in the parent.

The following is a chart which compares the color of the bracts of the new variety of plant of the present application with those of its antecedents and with other pink sports of its antecedents. However, the outstanding distinguishing characteristic of the new variety of plant is the rugose characteristic of the bracts, with the foliage not rugose, in combination with the light pink color of the bracts and the dark rose color of the venation.

Bract Color Comparison with Antecedents and Pink Sports of Antecedents

| Plant Patent No. | Plant Name | Color of Bracts (RHS) No. | (HCC) No. | (HCC) Name |
|---|---|---|---|---|
| (S.N. 2259) | Ott | Near 52D | 621 to 621/3 | Carmine Rose |
| (S.N. 2260) | Ott | Near 52D | 621 to 621/3 | Carmine Rose |
| 3392 | A. H. Supreme | 45D | 820/2 | Blood Red |
| 2962 | Annette Hegg | 47A | 821/2 | Currant Red |
| 3160 | A. H. Dark Red | 53B | 822/1 | Cardinal Red |
| 3099 | A. H. Pink | Near 47C | 020/2 | Delft Rose |
| 3120 | C-1 Pink | Near 47C | 020/2 | Delft Rose |
| 3738 | C-1 Hot Pink | 47D | 20/2 | Geranium Lake |

-continued

Bract Color Comparison with Antecedents and Pink Sports of Antecedents

| Plant Patent No. | Plant Name | Color of Bracts (RHS) No. | (HCC) No. | (HCC) Name |
|---|---|---|---|---|
| 3761 | A. H. Hot Pink | 52B | 21/1 | Carmine |

Note:
A. H. = Annette Hegg

What is claimed is:

1. A new and distinct variety of poinsettia plant, substantially as herein illustrated and described, the body of the bracts being a lighter pink than the parent U.S. Plant Pat. No. 3,392, the pink color being deeper with great illumination, and paling with less illumination, the venation being prominent and rose in color; characterized particularly in that the body of the bracts are rugose, i.e., the veins are sunken in valleys on the upper surface of the bract and the epidermis between veins is elevated or arched, the body of the bract being arched between opposite edges, the bracts being non-lobed and more round and less pointed than in the parent, the foliage being a lighter green than in the parent.

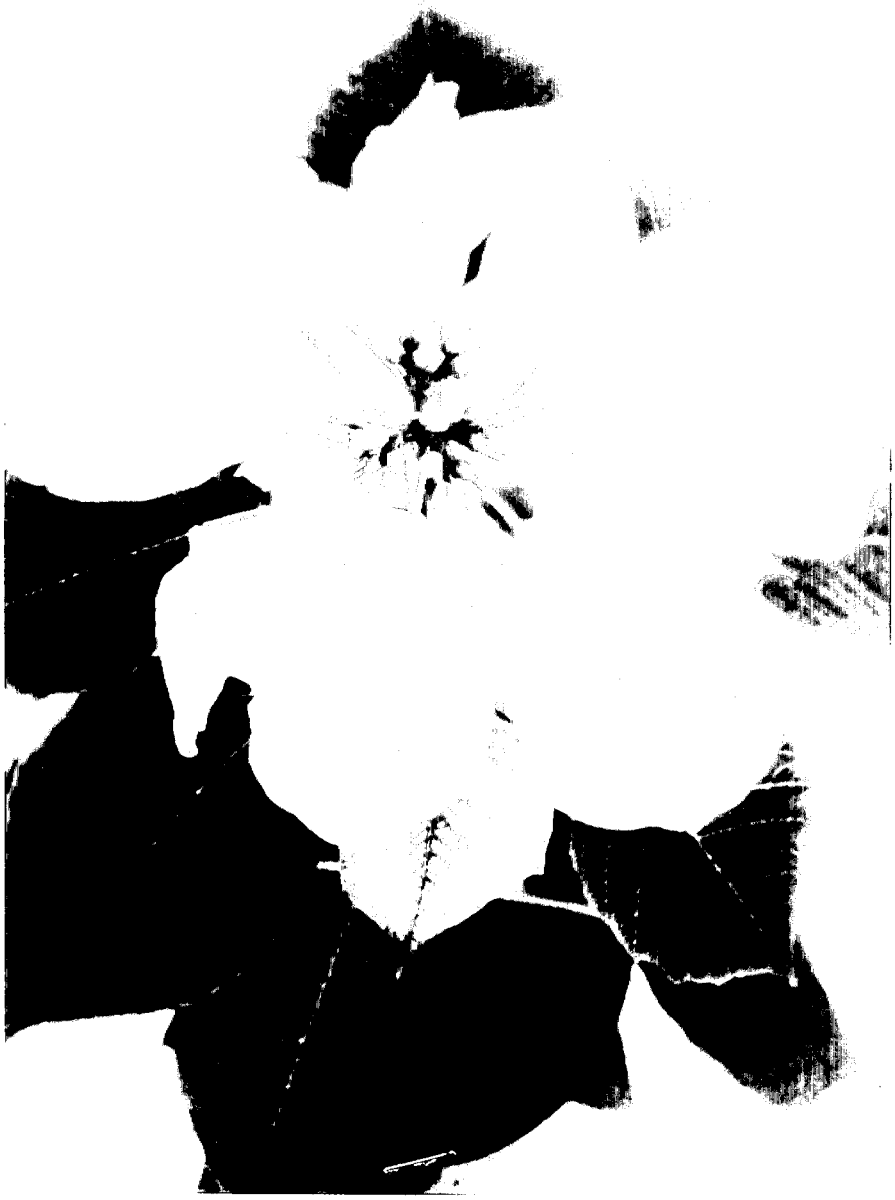

* * * * *